(12) United States Patent (10) Patent No.: US 9,491,559 B2
Anderson (45) Date of Patent: *Nov. 8, 2016

(54) METHOD AND APPARATUS FOR DIRECTIONAL ACOUSTIC FITTING OF HEARING AIDS

(71) Applicant: DEAN ROBERT GARY ANDERSON AS TRUSTEE OF THE D/L ANDERSON FAMILY TRUST, Orem, UT (US)

(72) Inventor: Dean Robert Gary Anderson, Orem, UT (US)

(73) Assignee: DEAN ROBERT GARY ANDERSON AS TRUSTEE OF THE D/L ANDERSON FAMILY TRUST, Orem (*) Notice: Subject to any disclaimer, the term of this patent is extended or adjusted under 35 U.S.C. 154(b) by 387 days.

This patent is subject to a terminal disclaimer.

(21) Appl. No.: 14/047,740

(22) Filed: Oct. 7, 2013

(65) Prior Publication Data

US 2014/0029775 A1  Jan. 30, 2014

Related U.S. Application Data

(63) Continuation of application No. 12/508,441, filed on Jul. 23, 2009, now Pat. No. 8,553,897.

(60) Provisional application No. 61/185,531, filed on Jun. 9, 2009.

(51) Int. Cl.
 *H04S 7/00* (2006.01)
 *A61B 5/11* (2006.01)
 (Continued)

(52) U.S. Cl.
 CPC .................. *H04S 7/301* (2013.01); *A61B 5/11* (2013.01); *A61B 5/6803* (2013.01); *H04R 25/70* (2013.01); *A61B 5/12* (2013.01); *H04R 25/40* (2013.01); *H04R 2430/03* (2013.01)

(58) Field of Classification Search
 None
 See application file for complete search history.

(56) References Cited

U.S. PATENT DOCUMENTS 3,385,937 A   5/1968  Lafon
5,197,332 A   3/1993  Shennib
(Continued)

FOREIGN PATENT DOCUMENTS

EP   1933590 A1   6/2008
GB   2394632 A    4/2004
(Continued)

OTHER PUBLICATIONS

Sakamoto et al.; "Frequency compression hearing aid for severe-to-profound hearing impairments"; Oct. 2000, Auris Nasus Larynx; vol. 27, Issue 4; pp. 327-334.

(Continued)

*Primary Examiner* — Curtis Kuntz
*Assistant Examiner* — Qin Zhu
(74) *Attorney, Agent, or Firm* — Morriss O'Bryant Compagni, P.C.

(57) ABSTRACT

A method of acoustically fitting a hearing aid comprises providing a plurality of audible tones, each having a predetermined frequency through stereo headphones. The tones are provided at specific sound pressure in each ear. The patient changes the relative sound pressure in each ear until a perceived direction of source of the tone is in front of the patient. The amplification or attenuation requirements of a hearing aid are modified based on the difference in the sound pressures required for the left and right ears of the patient for perceived directional sameness for each frequency band-pass channel.

22 Claims, 10 Drawing Sheets

(51) Int. Cl.
*A61B 5/00* (2006.01)
*A61B 5/12* (2006.01)
*H04R 25/00* (2006.01)

(56) References Cited

U.S. PATENT DOCUMENTS

| | | | |
|---|---|---|---|
| 5,325,436 | A | 6/1994 | Soli et al. |
| 5,396,560 | A | 3/1995 | Arcos et al. |
| 5,717,767 | A | 2/1998 | Inanaga et al. |
| 5,825,894 | A | 10/1998 | Shennib |
| 5,868,682 | A | 2/1999 | Combs et al. |
| 5,870,481 | A | 2/1999 | Dymond et al. |
| 5,878,146 | A | 3/1999 | Andersen |
| 5,923,764 | A | 7/1999 | Shennib |
| 6,118,875 | A | 9/2000 | Moller |
| 6,167,138 | A | 12/2000 | Shennib |
| 6,201,875 | B1 | 3/2001 | Davis et al. |
| 6,236,731 | B1 | 5/2001 | Brennan et al. |
| 6,389,142 | B1 | 5/2002 | Hagen et al. |
| 6,567,524 | B1 | 5/2003 | Svean et al. |
| 6,574,342 | B1 | 6/2003 | Davis et al. |
| 6,577,740 | B1 | 6/2003 | Bordewijk |
| 6,674,862 | B1 | 1/2004 | Magilen |
| 6,731,769 | B1 | 5/2004 | Lenhardt |
| 6,885,752 | B1 | 4/2005 | Chabries et al. |
| 6,912,289 | B2 | 6/2005 | Vonlanthen et al. |
| 7,058,188 | B1 | 6/2006 | Allred |
| 7,206,423 | B1 | 4/2007 | Feng et al. |
| 7,418,379 | B2 | 8/2008 | Vierthaler |
| 7,502,483 | B2 | 3/2009 | Rikimaru |
| 7,903,833 | B2 | 3/2011 | Goldberg et al. |
| 8,094,834 | B1 | 1/2012 | Brungart |
| 2002/0048374 | A1* | 4/2002 | Soli ............... H04R 25/30 381/60 |
| 2003/0142746 | A1 | 7/2003 | Tanaka et al. |
| 2004/0006283 | A1 | 1/2004 | Harrison et al. |
| 2004/0076301 | A1 | 4/2004 | Algazi et al. |
| 2006/0008102 | A1 | 1/2006 | Westergaard |
| 2006/0182294 | A1 | 8/2006 | Grasbon et al. |
| 2006/0204013 | A1 | 9/2006 | Hannibal et al. |
| 2006/0210090 | A1 | 9/2006 | Shennib |
| 2007/0127753 | A1 | 6/2007 | Feng et al. |
| 2007/0223720 | A1 | 9/2007 | Goldberg et al. |
| 2008/0121038 | A1* | 5/2008 | Davis ............... A61B 5/121 73/585 |
| 2009/0116657 | A1 | 5/2009 | Edwards et al. |
| 2009/0208024 | A1 | 8/2009 | Farber et al. |
| 2010/0310101 | A1 | 12/2010 | Anderson |
| 2011/0019846 | A1 | 1/2011 | Anderson |
| 2011/0075853 | A1 | 3/2011 | Anderson |
| 2011/0150256 | A1 | 6/2011 | Baechler et al. |
| 2011/0170711 | A1 | 7/2011 | Rettelbach et al. |
| 2013/0121517 | A1 | 5/2013 | Anderson |

FOREIGN PATENT DOCUMENTS

| | | |
|---|---|---|
| JP | 02503499 A | 10/1990 |
| JP | 2002159096 A | 5/2002 |
| WO | 2008141672 A1 | 11/2008 |

OTHER PUBLICATIONS

Alger, Alexandra. "A Chip in the Ear." Forbes. Nov. 2, 1998.
Gelfand, Stanley A. Essentials of Audiology, Third Edition, Mar. 2009, Thieme, pp. 250-253.
Edgar Villchur, "Signal Processing to Improve Speech Intelligibility in Perceptive Deafness", The Journal of the Acoustical Society of America, vol. 53, No. 6, 1973, pp. 1646-1657 (Abstract) (http://asadl.org/jasa/resource/1/jasman/v53/i6/p1646_s1?isAuthorized=no).
Ghent, Robert M., Jr. et al. "Interactive Binaurally Balanced Fittings for Improved Audibility, Reduced Costs, and Fewer Return Visits" The Hearing Review, Nov. 3, 2011.
Kraus, Eric M., MD, et al., "Envoy Esteem Totally Implantable Hearing System : Phase 2 Trial, 1-Year Hearing Results," Otolaryngology—Head and Neck Surgery, American Academy of Otolaryngology, Mar. 31, 2011.
Killion, Mead C. "Tribute: Edgar Villchur 1917-2011" The Hearing Review. Dec. 4, 2011.

\* cited by examiner

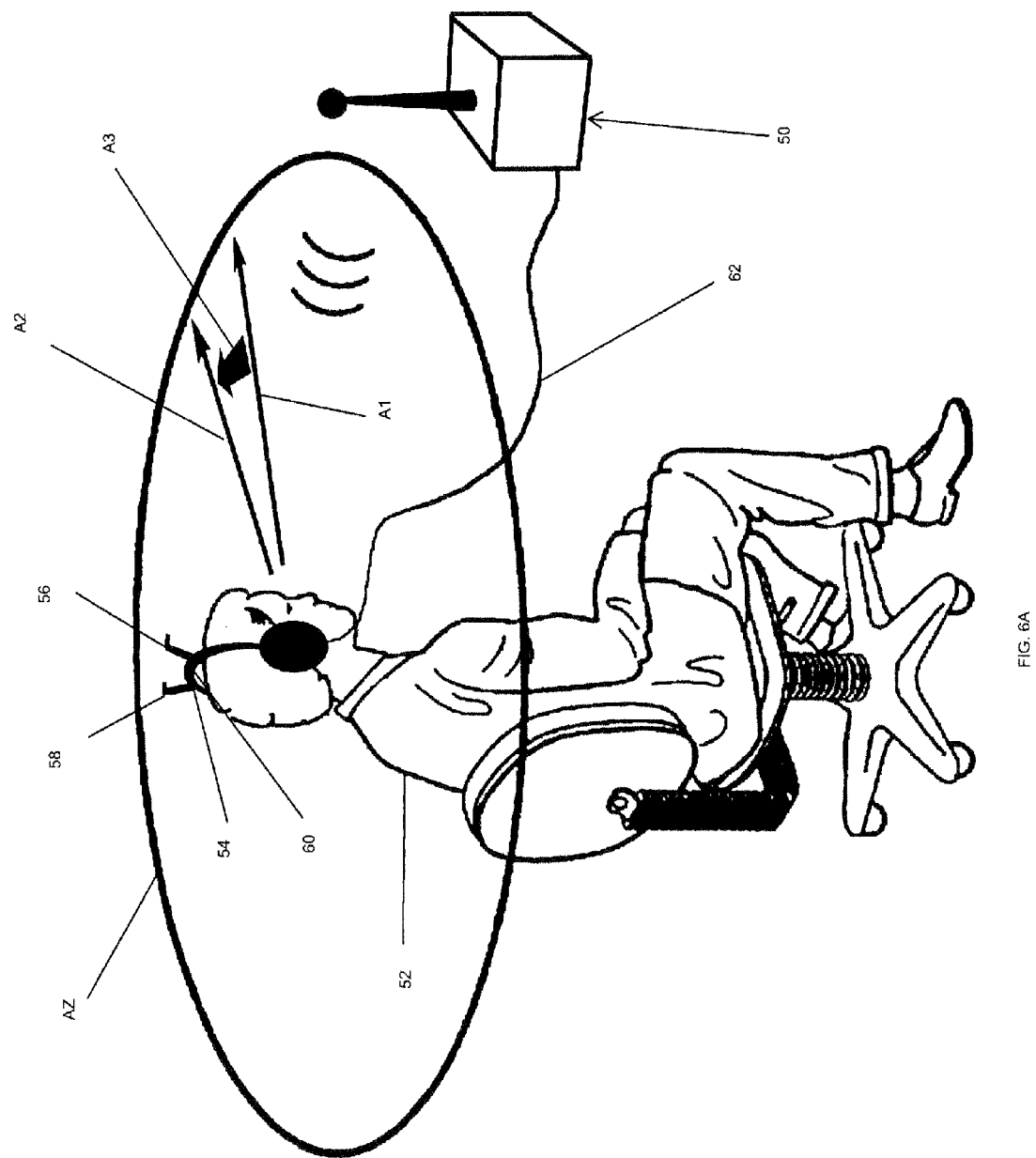

METHOD AND APPARATUS FOR DIRECTIONAL ACOUSTIC FITTING OF HEARING AIDS

CROSS-REFERENCE TO RELATED APPLICATION

This application is a continuation of U.S. patent application Ser. No. 12/508,441, filed on Jul. 23, 2009, now U.S. Pat. No. 8,553,897, which claims priority to U.S. Provisional Application Ser. No. 61/185,531, filed on Jun. 9, 2009, the entirety of each of which is incorporated by this reference.

BACKGROUND

Field of the Invention

The present invention relates generally to hearing aids used by the hearing impaired and methods for acoustically fitting such hearing aids based on the person's specific hearing capabilities at various sound frequencies and amplitudes. More specifically, the present invention relates to an apparatus and method for configuring or programming hearing aids based on the person's perceived position of sources of sounds at various frequencies and amplitudes.

State of the Art

Individuals with at least some hearing capacity can determine sound direction. When both ears are involved in this localization process (binaural hearing), sound direction is perceived by differences in both sound amplitude ("interaural amplitude difference") and slight timing variation ("interaural time difference") as well as audio diffraction for the ear that is closer to the sound source versus the shadowed ear. The process of sound localization also includes head movement to give affirmation of where the sound is coming from.

For individuals with normal hearing, the ability to perceive sound direction helps us to focus on a single conversation within a crowded and noisy room. Normal hearing individuals are typically able to converse (i.e., able to get 50% of words and 95% of sentences correct) at −5 dB signal-to-noise ("S/N") ratio in a noisy environment (e.g., 60 dB Sound Pressure Level ("$dB_{SPL}$")). Sound pressure is the local pressure deviation from the ambient (average, or equilibrium) pressure caused by a sound wave. The SI unit (International System of Units) for sound pressure is the pascal (symbol: Pa).

The instantaneous sound pressure is the deviation from the local ambient pressure $p_0$ caused by a sound wave at a given location and given instant in time. The effective sound pressure is the root mean square of the instantaneous sound pressure over a given interval of time (or space).

The sound pressure deviation (instantaneous acoustic pressure) p is:

$$p = \frac{F}{A}$$

where: F=force, A=area.

The entire pressure $p_{total}$ is:

$$p_{total} = p_0 + p$$

where: $p_0$=local ambient atmospheric (air) pressure, p=sound pressure deviation.

Sound pressure level (SPL) or sound level $L_p$ is a logarithmic measure of the rms sound pressure of a sound relative to a reference value. It is measured in decibels (dB) above a standard reference level.

$$L_p = 10\log_{10}\left(\frac{p_{rms}^2}{p_{ref}^2}\right) = 20\log_{10}\left(\frac{p_{rms}}{p_{ref}}\right) \text{ dB},$$

where: $p_{ref}$ is the reference sound pressure and $p_{rms}$ is the rms sound pressure being measured. The commonly used reference sound pressure in air is $p_{ref}$=20 µPa (rms), which is usually considered the threshold of human hearing (roughly the sound of a mosquito flying 3 m away).

Research has shown that the ear can also detect a time difference (i.e., delay) of sound of as little as 30 microseconds. For a typical adult-sized head, the time lag for sound waves travelling from one side of the head to the other is approximately 0.6 milliseconds. "Head shadow" refers to the attenuation and diffraction of sounds as they travel from one side of the head to the other. High frequency sounds are more affected by head shadow because of the shorter wavelength. The head shadow effect can be as much as 15 dB at 4000 Hz.

The "just noticeable difference" in azimuth perception for most normal hearing listeners when the sound source is straight ahead is a mere 1 degree. At lower frequency pulsed tones (i.e., below 1000 Hz) individuals with normal hearing have superior azimuth perception. Direction perception below 1000 Hz is predominantly a function of the person's ability to detect the slight timing variation that occurs between the left and right ears as the sound waves travel to the more distant ear. For higher continuous tone frequencies (i.e., between 1000 and 4000 Hz) a normal person can more easily detect changes in intensity. Sound direction localization for higher frequencies (between 1000 and 4000 Hz) is dominated by perception of differences in sound amplitude due to both an individual's frequency sensitivity and head shadow.

When sound comes from "off-angle" or to the side, the sound at each ear also "sounds" different. Sound to the furthest ear has to diffract (bend) around the head. Not only does the sound wave attenuate and arrive slightly later, but it is also altered in terms of the balance of high and low frequencies it contains (i.e., spectral alteration). Sounds with short wavelength (i.e., high frequency) do not diffract as well, so the furthest ear hears less of the high frequencies contained in the sound. The listener's brain detects this difference in frequency content, and uses the detected difference to locate the source of the sound. Head shadow diffraction also produces an overall diffraction modulation (i.e., interference patterns) for the shadowed ear.

In human speech, spoken vowels generate primarily low frequency sounds and spoken consonants generate primarily high frequency sounds. For an example, when the word "choose" is spoken, the "ch" and "z" sounds are formed by escaping air past the tongue, roof of the mouth, teeth and lips and have a rich high frequency spectrum (i.e., above 1000 Hz). These sounds are referred to as unvoiced sounds (e.g. fricatives, plosives). The "oo" sound is a voiced sound created by air motion sympathetic vibrations with the vocal cords and resonance within the lung/throat/mouth/nasal cavity and is typically below 1000 Hz. Thus, for speech recognition in the presence of ambient noise when aided by directional hearing or localization, the human binaural auditory system requires information perceived by differences in sound amplitude, slight timing variation and diffraction effects.

Head movement is also an important component of sound direction localization. The existence of ongoing spatial re-calibration in the human auditory system and accuracy is steadily reacquired with changes over time. Additionally, interaural time and level differences are not the only means by which one identifies the location of a sound source. Head movement, which results in sound changes in frequency, intensity and timing between the left and right ears assist the auditory system to locate the sound source.

Typically, a person with hearing degradation in one or both ears can still perceive sound direction. The use of hearings aids, however, will often times diminish the ability to perceive sound direction. Improper hearing aid fitting can further diminish sound direction perception. This is an obvious disadvantage to the use of hearing aids. Most often, others must raise their voice when talking to someone with hearing aids to communicate in a noisy environment.

The inability to clearly understand speech in a noisy environment is the most frequently reported complaint of hearing-impaired people that use hearing aids. Moreover, as hearing loss progresses, individuals require greater and greater signal-to-noise ratios in order to understand speech. It has been universally accepted through digital signal processing research that signal processing alone will not improve the intelligibility of a signal in noise, especially in the case where the signal is one person talking and the noise is other people talking (i.e., "the cocktail party effect"). With currently available hearing aids, there is no way to communicate to the digital processor that the listener now wishes to turn his/her attention from one talker to another, thereby reversing the roles of signal and noise sources.

While significant advances have been made in the last decade in hearing aid technology to improve the ability to hear conversations in noisy environments, such advances were often the result of the elimination of certain defects in hearing aid processing, such as distortion, limited bandwidth, peaks in the frequency response and improper automatic gain control ("ACG") action. Research conducted in the 1970's, before these defects were corrected, indicated that the wearer of hearing aids typically experienced an additional deficit of 5 to 10 dB above the unaided condition in the S/N required to understand speech. Normal hearing individuals wearing the same hearing aids also experienced a 5 to 10 dB deficit in the S/N required to carry on a conversation, indicating that the hearing aids were at fault.

As a result of diminished sound localization ability and the S/N levels for individuals wearing hearing aids in a noisy environment, most hearing aid wearers try to avoid such situations or end up removing the hearing aids in order to regain the ability to focus on a particular conversation, despite the subsequent loss of understanding in portions of what is often perceived as muffled conversation. In order for hearing impaired individuals to be able to hear discrete conversations in a noisy environment, an increase in S/N is required, even when no defects in the hearing aid processing exist. Those with mild hearing loss typically need about 2 to 3 dB greater S/N than those with normal hearing. Those with moderate hearing loss typically need 5 to 7 dB greater S/N, and those with severe hearing loss typically need a 9 to 12 dB increase in S/N.

One attempt in the art to improve S/N in hearing aids is through the use of directional microphones. Because directional microphones are subject to the effects of back and/or side lobes, a deficiency in such hearing aids is a result of these effects in directional microphone sound reception. As a result, a person wearing hearing aids with directional microphones, sometimes ends up primarily hearing the conversation behind him/her through the back lobe of the directional microphone.

Another deficiency in the current state of hearing aids related to improving speech recognition in noisy environments is directly related to the current fitting protocols used to acoustically fit hearing aids to a hearing impaired individual. The current fitting process often results in substantial loss of localization perception for the user by making only a fraction of the speech cues available. In addition, the maximum loudness discomfort levels of the patient are not measured or accounted for in current hearing aid fitting protocols.

The basic signal processing architecture set forth in U.S. Pat. No. 6,885,752 to Chabries, et al. is representative of most modern hearing aids and uses multi-band, multiplicative compression. The band-pass filters typically generate nine or more fixed channels with band-pass resolutions spaced at half octaves or less between 200 Hz and 12,000 Hz.

In each frequency band, non-linear amplification or gain (referred to as multiplicative compression) is applied to each channel individually. As set forth in U.S. Pat. No. 6,885,752, one factor in restoring hearing for individuals with hearing losses is to provide the appropriate gain. For each frequency band where hearing has deviated from normal, a different multiplicative compression is supplied to make the greatest use of the individual's remaining hearing sensation. The multi-band, multiplicative AGC adaptive compression approach used in U.S. Pat. No. 6,885,752 and most modern hearing aids has no explicit feedback or feed forward.

Assessment of hearing is the first step in the prescribing and acoustic fitting of a hearing aid. Accurate assessment of the individual's hearing function is important because all hearing aid prescriptive formulas depend on one or more sets of hearing diagnostic data. Well known methods of acoustically fitting a hearing aid to an individual begin with the measurement of the threshold of the individual's hearing by using a calibrated sound-stimulus-producing device and calibrated headphones. The measurement of the threshold of hearing takes place in an isolated sound room. It is usually a room where there is very little audible noise. The sound-stimulus-producing device and the calibrated headphones used in the testing are typically referred to as an "audiometer."

Generally, the audiometer generates pure tones, warbled tones, swept tones or band-pass noise centered at various frequencies between 125 Hz and 12,000 Hz that are representative of the frequency bands or channels designed within the hearing aid. These tones are transmitted through the headphones of the audiometer to the individual being tested. The intensity or volume of each tone is varied until the individual can just barely detect the presence of the tone. For each tone, the intensity of the tone at which the individual can just barely detect the presence of the tone, is known as the individual's air conduction threshold of hearing. Although the threshold of hearing is only one element among several that characterizes an individual's hearing loss, it is the predominant measure traditionally used to acoustically fit a hearing compensation device.

The usable range of hearing (also called the dynamic range) is usually characterized along coordinates of frequency and sound pressure level and falls between an area bounded by the audibility curve (or threshold of hearing) and the Loudness Discomfort Level (LDL), which are sounds too loud to listen to in comfort or are unpleasant or are painful. Many hearing aid fitting protocols include the measurement of the Loudness Discomfort Level as a function of frequency.

Examples of more advanced protocols are set forth in U.S. Pat. Nos. 6,201,875 and 6,574,342. These patents disclose a system where curves are generated for a series of different loudness levels (or loudness contours) such as contours for: Uncomfortably Loud, Loud but OK, Comfortable but Slightly Loud, Comfortable, Comfortable but Slightly Soft, Soft, and Very Soft. Also disclosed is a system to dynamically change the non-linear gain for each frequency channel based on the family of curves.

Once the threshold of hearing in each frequency band has been determined, this threshold of hearing is used to estimate the amount of amplification, compression, and/or other adjustment that will be employed to compensate for the individual's loss of hearing. The implementation of the amplification, compression, and/or other adjustments and the hearing compensation achieved thereby depends upon the hearing compensation device being employed. There are various formulas known in the art which have been used to estimate the acoustic parameters based upon the observed threshold of hearing. These include industry hearing compensation device formulas known as NAL1, NAL2, and POGO. There are also various proprietary methods used by various hearing-aid manufacturers. Additionally, based upon the experience of the person performing the testing and the fitting of the hearing-aid to the individual, these various formulas may be adjusted. The appropriate gain calculated for each frequency channel may also include considerations and adjustments for the additional measurements of loudness discomfort level or other measured loudness contours. The appropriate gain calculated for each frequency channel then becomes the hearing compensation curve or look-up table data programmed into the hearing aid for each frequency channel. Programming the hearing aid memory for the hearing aid digital signal processor (DSP) may be done dynamically during the fitting process with devices such as the GN Otometrics HI-PRO programming interface so that changes to the hearing compensation curves or look-up table data may be evaluated immediately by the person being fitted and the audiologist.

Another condition associated with sensorineural hearing loss is loudness recruiting. Loudness recruitment is a condition that results in an abnormally-rapid increase in loudness perception with relatively small increases in sound levels above the hearing threshold of the hearing impaired person. Recruitment is a common characteristic of hearing loss that results from damage to the sensory cells of the cochlea, the most common type of sensory hearing loss. For example, a person with loudness recruitment may not be able to hear high frequency sounds below 50 $dB_{SPL}$, but may find any sounds above 80 $dB_{SPL}$ uncomfortable and even distorted. For such a hearing impaired individual, recruitment can mean a collapse of loudness tolerance and the feeling of distortion of loud sounds.

Recruitment is always a by-product of a sensorineural hearing loss. Recruitment is usually due to a reduction in neural elements associated with the inner ear hair cells. This phenomenon occurs because at some decibel level, the normal hair cells adjacent to the damaged hair cells (corresponding to the frequency of a hearing loss) are "recruited." At the decibel level at which these recruited hair cells are triggered, the perceived loudness quickly increases and often causes hearing discomfort.

A known test for recruitment is Alternate Binaural Loudness Balancing (ABLB). ABLB compares the relative loudness of a series of tones presented alternately to each ear. In practice the ABLB test is rarely performed by audiologist while fitting hearing aids because of the time it takes to perform such tests using current testing methods and devices and the lack of use of such test result data by current systems for hearing aid fitting.

As current methods of hearing aid fitting do not typically account for loudness recruitment, patients having such a condition are often fitted with hearing aids that become uncomfortable to wear because the dynamic range of hearing is so easily exceeded by the hearing aid. In such cases, the only option is for the patient to manually turn the volume down on the hearing aid, which universally reduces the amplification for all frequencies and across all sound levels.

The goal of any hearing aid is to amplify or otherwise process sounds so that they can be comfortably heard and understood. For larger degrees of hearing loss involving loudness recruitment where even everyday speech communication is difficult, amplification is required. Amplification that is sufficient to make sub-threshold sounds audible, however, will tend to make higher-level sounds uncomfortably loud. Often gain compression techniques are employed to compensate for this problem. It is commonly believed in the art; however, that even with the best methods of compression, it is inevitable that hearing-aid amplified sounds will be at least somewhat louder than they would be for a normal-hearing person for some input levels. In addition, because of the techniques employed in current hearing testing systems, it is also the case that the best amplification compression methods will not be properly configured for a given patent because the patient has not been properly tested in order to generate the correct gain curves for the hearing aids.

Current methods of hearing aid fitting employ the use of subjective listening methods and interpretation of the test results, which typically rely on verbal communications of sound perception relayed between the patient and an audiologist administering the test. Patients' ability to quantify perceived loudness of a tone also varies by individual, especially when current testing methods may supply tones to each ear at spaced apart intervals or between hearing tests that are often several seconds apart. As such, a major deficiency of most hearing aid fitting protocols is the inaccurate test results that are often attained that are used as the basis for a hearing aid fitting.

Indeed, when such verbal test methods are used, discrepancies of 10 dB or more are not uncommon and have been reported to be found in 36% of threshold of hearing measurements. A typical binaural fitting of digital hearing aids having 9 band-pass channels requires a minimum of 18 hearing threshold measurements. Based on the known error rate of 36%, it is the case that six or seven measurements in such a test are likely in error.

Another major disadvantage of measurements obtained using a traditional transducer is that results are not interchangeable with measurements taken with another transducer for a given individual.

Still another deficiency of current audiometers is found within the audiometer standards. (See Specification of Audiometers, ANSI-S3.6-1989, American 45 Standards National Institute, the entirety of which is incorporated by this reference). For example, in speech audiometry evaluation, the speech stimuli level is adjusted for one ear and speech noise level (or masking) is separately adjusted in the opposite ear. Bilateral, asymmetric hearing loss is far more prevalent than symmetrical loss. Asymmetric hearing loss requires different hearing compensation curves for each ear.

Moreover, spectral group velocities can shift and distort based on frequency and amplitude weighting and amplification through the non-ideal hearing aid components (for example: damping via ferrofluids purposely designed into some receiver-speakers to reduce unintended oscillations).

Accordingly, it would be advantageous to provide hearing aids and a hearing aid fitting system and method that provide increased signal to noise ratios. It would be a further advantage to provide hearing aids and a hearing aid fitting system and method that eliminates the need for fitting by a trained audiologist. It would be another advantage to provide hearing aids and a hearing aid fitting system and method that significantly reduces the smearing of directional information. It would be a further advantage to provide hearing aids and a hearing aid fitting system that compensates for loudness recruitment. These and other advantages are provided by hearing aids and a hearing aid fitting system and method according to the present invention set forth hereinafter by incorporating head azimuth detection during the fitting process.

SUMMARY OF THE INVENTION

Accordingly, the present invention overcomes many of the deficiencies and disadvantages of prior art hearing aid technologies and hearing aid fitting systems and methods by incorporating precise sound localization into an acoustic hearing aid fitting process. The present invention uses sound direction affirmation by the person being fitted through the use of near instantaneous head azimuth detection and measurement. Head azimuth is used to provide near instantaneous modification of discrete sound channel information during the hearing evaluation and hearing aid fitting to coordinate directional hearing cues for the hearing aid fitted individual. Sound localization is repeated for a broad range of sound frequencies and/or sound intensities. The resulting data is recorded and used to program the hearing aid(s) according to the person's sound localization responses. As a result, the azimuth direction sensed for all frequency and gain compensation channels of the hearing aid(s) results in directional sameness across the entire spectrum of audible sounds.

In one embodiment of the hearing aid fitting system, a pair of stereo headphones is adapted to measure azimuth orientation of the subject's head relative to an arbitrary initial horizontal direction. Signal processing is added to each of the stereo headphone channels to enable alterations of sound amplitude, sound phase, channel timing delay and/or head audio diffraction modulation. The differential sound amplitudes, sound phase, channel delays and/or modulation are synchronized with the headphone azimuth orientation by a processor to simulate the results of directional hearing so that the simulated sound source yields "affirmation" to the individual being tested with even the slightest of head movements. The angular update rate and channel processing are sufficiently fast so that the perceived sound image does not suffer from lag or source position jumping.

Continuous or pulsed tones that are pure, warbled, swept or band-pass noise are supplied to the stereo headphone channels. The individual is asked to simply turn his/her head or rotate a swivel chair upon which the individual is sitting to the direction of the sound source until he/she feels that he/she is accurately and directly facing the source (i.e., the perceived sound in both ears has been equalized). The corresponding sound pressures used for each ear to achieve directional balance for each tone in the series of audible tones at various frequencies and intensities are then recorded.

Simulated azimuth orientation of the sound source may also be varied to insure that the "correct" azimuth orientation is somewhat random and the test subject does not feel that there is any particular "correct" orientation point in the room. A computer measures the error in azimuth and adjusts each channel volume, phase and/or delay (for pulsed tones) accordingly.

Variation of the amplitudes of the continuous tones allows the software to determine the proper amplification for each ear for each frequency. The individual being tested only needs to turn his/her head or chair until he/she is facing his/her perception of the sound source direction.

Variation in channel delay can also be used to calibrate programmable frequency band delay correction for digital hearings aids including this feature. The purpose of the programmable frequency band delay correction is to sharpen directional response sensed by the hearing aid fitted individual so that delay corrections and amplitude corrections align to create directional sameness.

In one embodiment of the present invention, on-going gain compensation reprogramming and/or channel delay reprogramming of the hearing aid during the fitting process is provided.

The present invention uses near instantaneous head azimuth measurement and modification of sound channel information to coordinate directional hearing cues during the hearing aid fitting process. The result is that the azimuth direction sensed for all frequency channels of the hearing aid(s) results in directional sameness. The process may first be performed without the person wearing hearing aids in order to initially program the hearing aids according to the person's measured hearing deficiencies. Once programmed, the process can be repeated with the person wearing the hearing aids in order to fine tune the hearing aids.

In another embodiment of the present invention, head azimuth detection is employed to measure sound pressure for loudness balancing of a patient being fitted for hearing aids. The corresponding gain requirements are then used to calibrate compression protocols for the hearing aid in order to adjust the amplification of the hearing aids to compensate for loudness recruitment.

The present invention also provides a hearing aid that is programmed to respond to changes in the individual hearing aid volume controls by selectively switching between a family of coordinated hearing compensation curves in order to continue azimuth directional sameness at a variety of user adjusted amplification levels.

A hearing aid according to the present invention is also capable of being programmed by the wearer without the need for an audiologist to be present. The fitting system and method may include computer, software, and headphones containing an azimuth detector. The software would produce a series of audible tones at various frequencies and intensities. The software would then use the azimuth data with corresponding differential sound pressure requirements recording during the sound localization process to program the gain curves of the hearing aids. It is possible that the hearing aids can be reprogrammed remotely while the user is wearing headphones through which an auditory signal is sent to program the hearing aids. With the sophistication of current sound card technology and modern headphone designs, precise calibration of the headphones to actual sound pressure levels may not be a requirement if the wearer can iteratively repeat the testing and fitting process until he achieves maximum comfort and speech understanding in the presence of noise with the hearing aid(s) during an adjustment period.

By providing directional fitting into a hearing aid fitting protocol according to the present invention, a signal-to-noise ratio improvement of 3 dB or greater is possible. Moreover, the addition of directional microphones to the hearing aid may yield and result in "super-hearing" to the correctly fitted individual.

According to the present invention, head movement is used for precise auditory localization to accurately determine an individual's perception of loudness differences and threshold of hearing at various frequencies. In addition, the head azimuth is more accurately measured by a computer system, as opposed to the prior art method of using verbal communications of sound perception relayed between the individual being tested and the audiologist.

The present invention uses head movement information in conjunction with differential sound amplitude and/or timing variation for the purposes of hearing aid fitting. Including head movement information in the hearing aid fitting environment is more ergonomically efficient and accurate and results in a superior fitting and significantly higher user satisfaction.

In another embodiment of the present invention, the patient uses a user controllable interface, such as a joystick, dial, or slide pot, to equalize the sound between the left and right ears for each set of tones presented to the ears. Thus, rather than moving the head, the user accomplishes the same effect by adjusting the gain until the tone level in both ears is perceived as being equal.

The foregoing advantages and characterizing features will become apparent from the following description of certain illustrative embodiments of the invention. The above-described features and advantages of the present invention, as well as additional features and advantages, will be set forth or will become more fully apparent in the detailed description that follows and in the appended claims. The novel features which are considered characteristic of this invention are set forth in the attached claims. Furthermore, the features and advantages of the present invention may be learned by the practice of the invention, or will be obvious to one skilled in the art from the description, as set forth hereinafter.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 6A is a perspective drawing of a second embodiment of a hearing aid fitting system and a subject person using the system in accordance with the principles of the present invention.

DETAILED DESCRIPTION OF THE ILLUSTRATED EMBODIMENTS

Those of ordinary skill in the art will realize that the following description of the present invention is illustrative only and not in any way limiting. Other embodiments of the invention will readily suggest themselves to such skilled persons.

Figure 1:
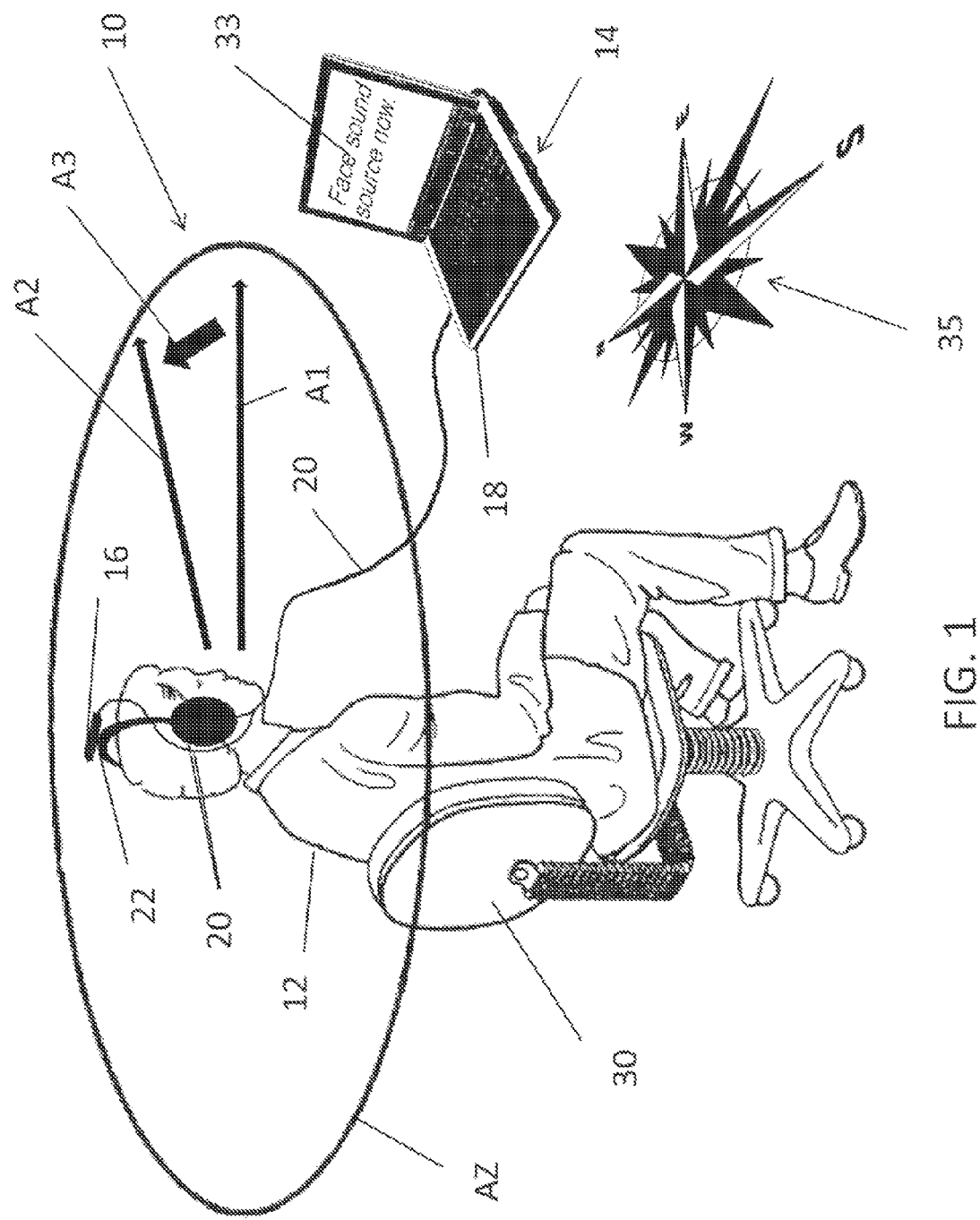
FIG. 1 is a perspective drawing of a first embodiment of a hearing aid fitting system and a subject person using the system in accordance with the principles of the present invention.

FIG. 1 illustrates a hearing aid fitting system, generally indicated at 10 in accordance with the principles of the present invention. An assessment of sound direction perception of an individual 12 is accurately made across a broad dynamic range in multiple frequency bands. Unlike prior art fitting systems, the tones presented to the individual 12 in the hearing loss assessment and fitting system 10 of the present invention are generated by an audiometer 14, which includes a head azimuth detecting device 16 that is measured in near real time by a computer 18 or other processing device that also provides corresponding binaural feedback and affirmation to the individual being fitted via a pair of headphones 20. The present hearing aid fitting system 10 coordinates directional perception sameness between the multiple frequency bands and across the wide dynamic range of the fitted hearing aids to improve speech understanding in noisy environments.

According to the present invention, the fitting system 10 transmits an audible tone through the headphones 20 in order to cause the individual 12 to localize the source of the tone. The tone is in stereo such that the tone will have a different intensity, delay (for pulsed tones) and/or phase, depending on the current head azimuth position, as illustrated by arrow A1, in each ear. The arrow A1 represents the individual's current head azimuth during the localization process as the individual searches for the sound source. The second arrow A2 represents the individual's final localization determination. The third arrow A3 represents the head azimuth error as measured in the search process. While the azimuth plane is represented by ring AZ, the system may only have the individual search within a 30 to 45 degree arc for all generated tones. Because the localization perception of most individuals is rather precise, it is not necessary to require the individual 12 to search for tones over a larger azimuth range. The compass rose 35 represents the local magnetic field.

Figure 2:
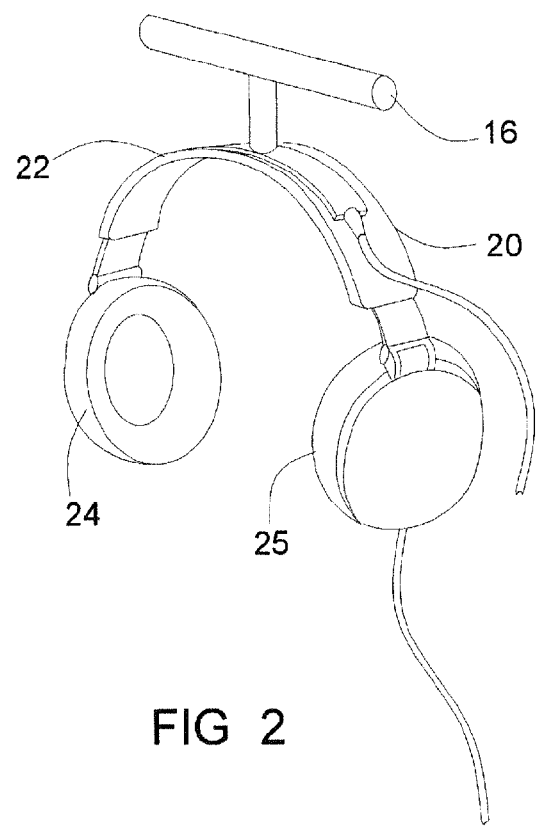
FIG. 2 is a perspective view of a first embodiment of headphones containing an azimuth detector in accordance with the principles of the present invention.

As shown in FIG. 2, the headphones 20 include the azimuth measuring device 16 attached to the head strap 22. One such azimuth measuring device is a 2-axis digital integrated compass solution such as the Honeywell HMC6352. A 3-axis compass solution could also be used. The azimuth measuring device may contain a USB (Universal Serial Bus) interface that is directly coupled to the computer 18 (see FIG. 1). That way, data from the azimuth device 16 is near instantaneously read and used to calibrate the audio signals sent to the individual 12 based on the real-time head azimuth AZ of the individual 12. The headphones are calibrated to ensure that each ear piece 24 and 25 (see FIG. 2) are precisely equalized relative to each other and thus ensure that any head movement or other recordable response to audio signals from the headphones 20 by the individual 12 is accurate.

Figure 3:
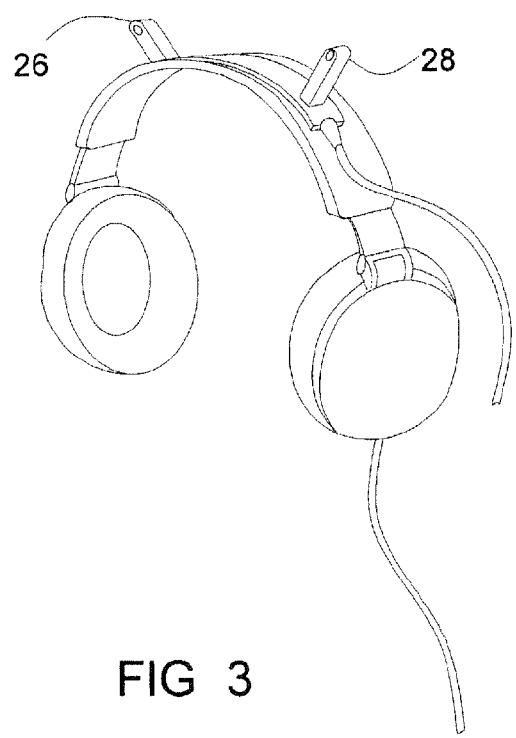
FIG. 3 is a perspective view of a second embodiment of headphones containing an azimuth detector in accordance with the principles of the present invention.

As shown in FIG. 3, it is also contemplated that two ultrasonic receivers 26 and 28 attached to the head strap 22 could be used in place of the digital compass 16 shown in FIG. 2. Ultrasonic receivers 26 and 28 can be used to measure the differential in the pulse time-of-flight in a dual ranging system and this differential measurement can be used to detect and calculate head position azimuth using principles known in the art. Beam-modulation telemetry or interferometric or other methods may also be used. Laser range measurement systems, mechanically affixed optical encoders or other types of azimuth measurement devices may also be employed. Those of skill in the art will appreciate that there may be many devices and methods for detecting head azimuth, all of which are contemplated for use with the present invention. For example, the use of a digital camera coupled to the computer 18 could be used to detect head azimuth by using face recognition-type software. As the individual's head swivels, the spacing between eyes or other facial features could be measured and used to determine head azimuth. It is also contemplated that high contrast optical targets or light sources might be affixed to the head phones and used to determine head azimuth by measuring separation changes with a camera and computer. It is also contemplated within the spirit and scope of the present invention that the detection of side-to-side eye movement could also be employed to determine perceived sound localization. That is, the same processes could be employed to create the appropriate gain curves for each frequency by using eye movement as the source of sound localization determination without the need for the user to move his or her head.

As shown in FIGS. 2 and 3, the azimuth sensors are physically attached to the headphones. Alternatively, the components of the azimuth sensor could the attached separately to the individuals head as to be separate from the headphones.

Referring again to FIG. 1, it is desirable that the angular update rate of the azimuth measuring device and channel processing through the computer 18 are sufficiently fast so that the perceived sound image in the headphones 20 does not suffer from lag or source position jumping. As illustrated, the personal computer 18 is used to generate or playback audio test stimulus to the individual 12, power and process the azimuth sensor 16, process and coordinate the headphone volumes, generate signals for dynamic programming of the hearing aids, perform test coordination, and/or other functions described herein. The individual 20 is shown seated on a swivel chair 30. The interconnecting cable 32 contains wiring for the stereo headphone channels, a USB interface for the azimuth detector 16, and possibly dual hearing aid programming signals.

Programming of the hearing aids (not visible) may be performed using audio encoding techniques as set forth herein. The hearing aid fitting protocol incorporating sound direction perception of the present invention ([hereinafter "the protocol") requires that the individual being fitted has some degree of hearing in both ears. The individual 12 being fitted is placed in a low noise environment (<30 dB$_{SPL}$) without hearing aids and a set of calibrated stereo (e.g., circumaural) headphones 20 with azimuth sensing means 16 is positioned on the individual's head and over the individual's ears. The individual 12 is seated in a swivel chair 30 and is generally facing in a forward direction. The overall volume or amplification is individually adjusted for each side of the headphones 20 until the individual 12 can understand the test giver's (not shown) oral instructions in comfort (which would corresponded to a normal hearing person's perception of speech in the range of 40 to 60 dB$_{SPL}$ when measured at 1 meter distance). It is noted that the test giver may comprise computer software installed on the computer 18 that includes voice cues and/or written cues 33 (e.g., the written cues "Face sound source now." Illustrated on the computer 18) for the individual 12 to complete the protocol. The overall sound pressure level required to produce comfortable hearing is then approximated for each ear based on the input volume adjustment and amplification required to achieve this comfortable hearing level. The Loudness Discomfort Levels and Thresholds of Hearing for each frequency channel are then measured as a function of sound pressure in order to determine the overall dynamic range of hearing and to determine appropriate directional test levels to record. Based on the data recorded by the computer 18 during the test, the system 14 generates the appropriate gain for each individual frequency channel. The gain may be a function of Input dB$_{SPL}$ versus Output dB$_{SPL}$ or Input dB$_{SPL}$ versus Gain dB. The appropriate gain for each frequency channel may be different and the appropriate gain for each frequency channel for each ear may be different. These curves are generally referred to as "hearing compensation curves." It is important to note that the data may not be linear and that the output or gain is typically some function of the input. This data is derived by audiometric protocols provided in the computer software. Thus, upon completion of the test, a family of gain curves or data points are produced for each frequency and can then be programmed into the hearing aid. Reprogramming of each hearing aid can occur at the end of each test.

For hearing aids that use a "look-up" table for required gain for specific frequencies and input intensities, interpolation protocols are programmed into the hearing aid to accommodate frequencies and input intensities between specific data points.

Hearing aids with dynamic programming means individually available or attached to each hearing aid may be programmed for each ear based on the previous required gain estimations. The hearing aids with dynamic programming means may be then positioned appropriately into the individual's ears and the headphones are again placed so as to encompass the individual's ears and the hearing aids. Any adjustment deemed required to increase or decrease the individual's hearing aid amplification for comfortable listening to the tester's speech is again made by reprogramming each hearing aid.

The overall directional testing process begins with a continuous stereo tone delivered to the Headphones at a comfortable sound pressure level between the previously determined LDLs and hearing thresholds (e.g., 70 dB$_{SPL}$). The tone may be warbled rather than using a single frequency tone so that the tone does not stay parked directly on a potential resonance frequency of one of the hearing aid receivers. The warbled tone is restricted to frequencies within the bandwidth of one of the hearing aid band-pass channels.

Figure 4:
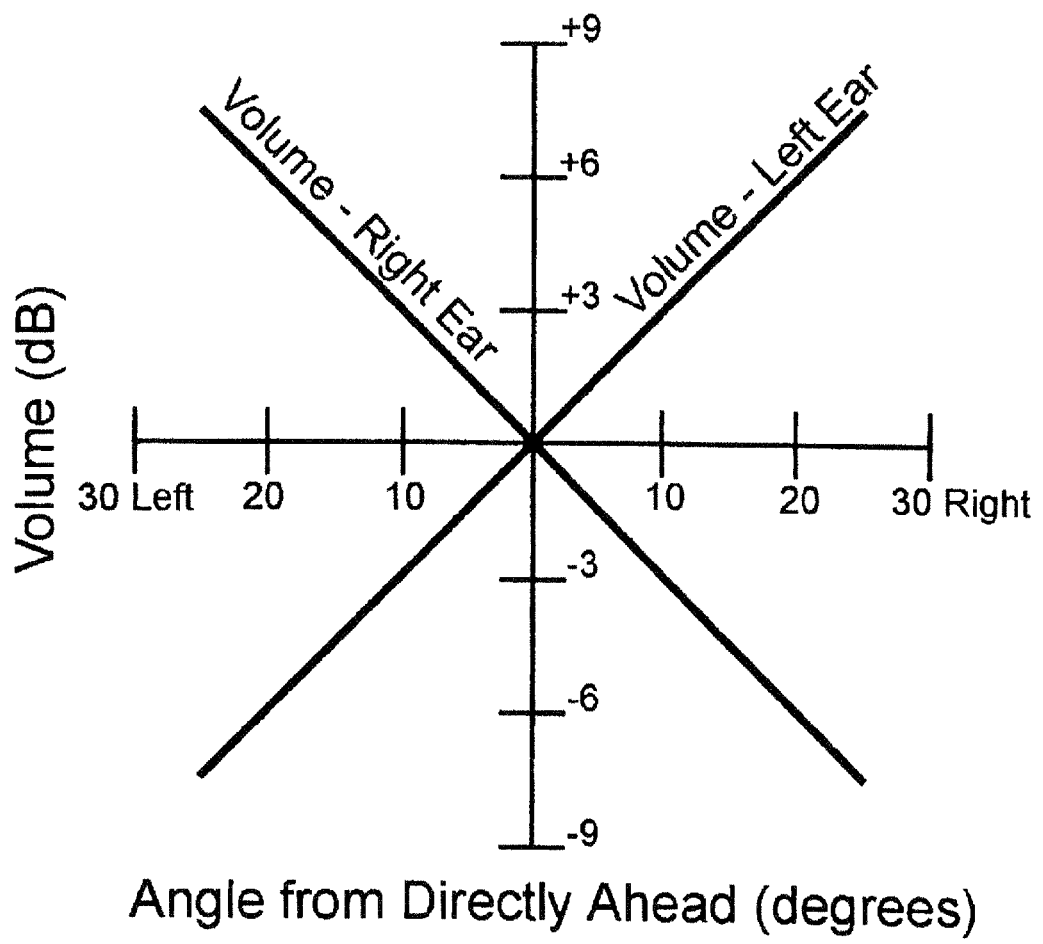
FIG. 4 is a graphical representation of left and right ear volumes versus azimuth angle.

The volume of each stereo channel is controlled in such a manner as to continuously simulate directional hearing as a function of the individual's actual head azimuth position. The simulation is accomplished by establishing an arbitrary "correct" azimuth for a simulated sound source where the loudness levels for each side of the headphones will correspond to the current azimuth offset of the simulated source. For example, consider an azimuth source directly ahead of the individual. As the individual turns his/her head to the left, the tone volume will increase in the right ear and decrease in the left ear. As the individual turns his/her head to the right, the tone volume will increase in the left ear and decrease in the right ear. This directional hearing processing based on the individual's actual head azimuth is illustrated in FIG. 4. The change in tone volumes versus change in angle is arbitrarily drawn and other slopes may be used to increase azimuth directional accuracy or sensitivity of the overall fitting system.

A random azimuth direction may be arbitrarily selected for each subsequent measurement. A random direction is used so that the individual does not anticipate any particular "correct" test direction orientation. The random direction is perhaps +/−20 degrees from the general room testing orientation so that the directional sensor remains at an orientation enabling greatest accuracy and so the individual does not strain with excessive head searching or chair reorientation.

The individual is instructed to simply "look" towards the direction of the sound source. The individual is instructed to close his/her eyes if desired. The individual is told to use a head searching motion to help seek the sound source. The individual is told that he/she may wish to swivel his chair if needed. The individual is told that there is no "correct" direction and that the azimuth locations will be varied during the test. The individual is coaxed to use the instinctual processes of localization and affirmation to determine the direction of the sound source.

The testing system of the present invention provides a game-like quality that results in more accurate test results because the individual becomes more involved in the testing process. As the test progresses, the individual will become more adept in the process of seeking the sound source and will quickly get the hang of it with just a few tests in most cases. Each test may only require a few seconds to complete as the full test series progresses before the individual finalizes each of his/her sound source decisions.

Figure 5:
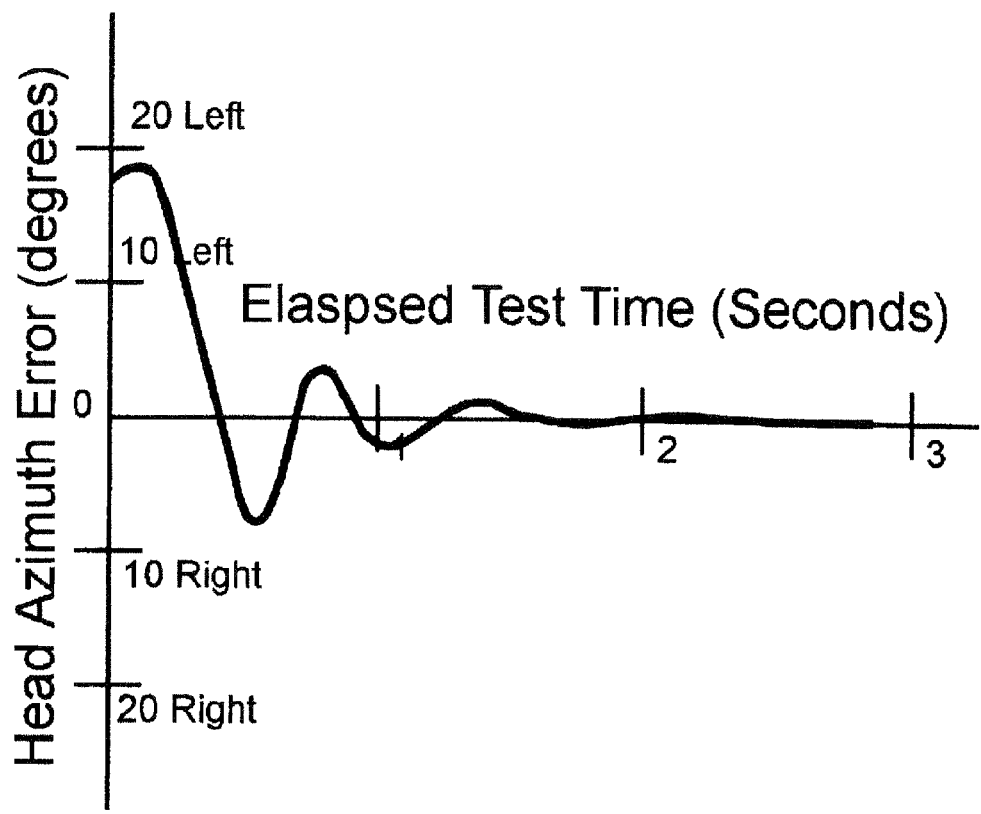
FIG. 5 is a graphical representation of head azimuth error versus the elapsed test time.

The graph set forth in FIG. 5 represents a head azimuth search. The azimuth error is a measurement of azimuth difference from the individual's final decision for his/her perception of the "correct" localization and the current azimuth location. The tester can even watch the individual's localization process to determine when the individual has made his/her final localization determination.

As shown in FIG. 6A, an individual's head azimuth AZ is measured using an ultrasonic azimuth detection system 50. One arrow A1 represents the individual's current head azimuth AZ during the localization process as the individual 52 searches for the sound source. The second arrow A2 represents the individual's final localization determination. The third arrow A3 represents the head azimuth error as measured in the search process. The headphones 54 are shown with 2 ultrasonic receivers 56 and 58 attached to the head strap 60. The ultrasonic receivers 56 and 58 are used to measure the differential in the pulse time-of-flight in a dual ranging system and this differential measurement is used to detect and calculate head position azimuth AZ using principles commonly known in the art. The interconnecting cable 62 contains wiring for the stereo headphone channels, the differential ultrasonic detectors 56 and 58, and the dual hearing aid programming signals and the dual hearing aid drive power (if required). The ultrasonic receivers 56 and 58 are in a fixed orientation relative to the axis formed by the axis established by the intersecting line between the headphone speakers. The ultrasonic receivers are spaced at a known distance and sufficiently far apart as to yield azimuth measurement accuracy of 1 degree or better.

Figure 6B:
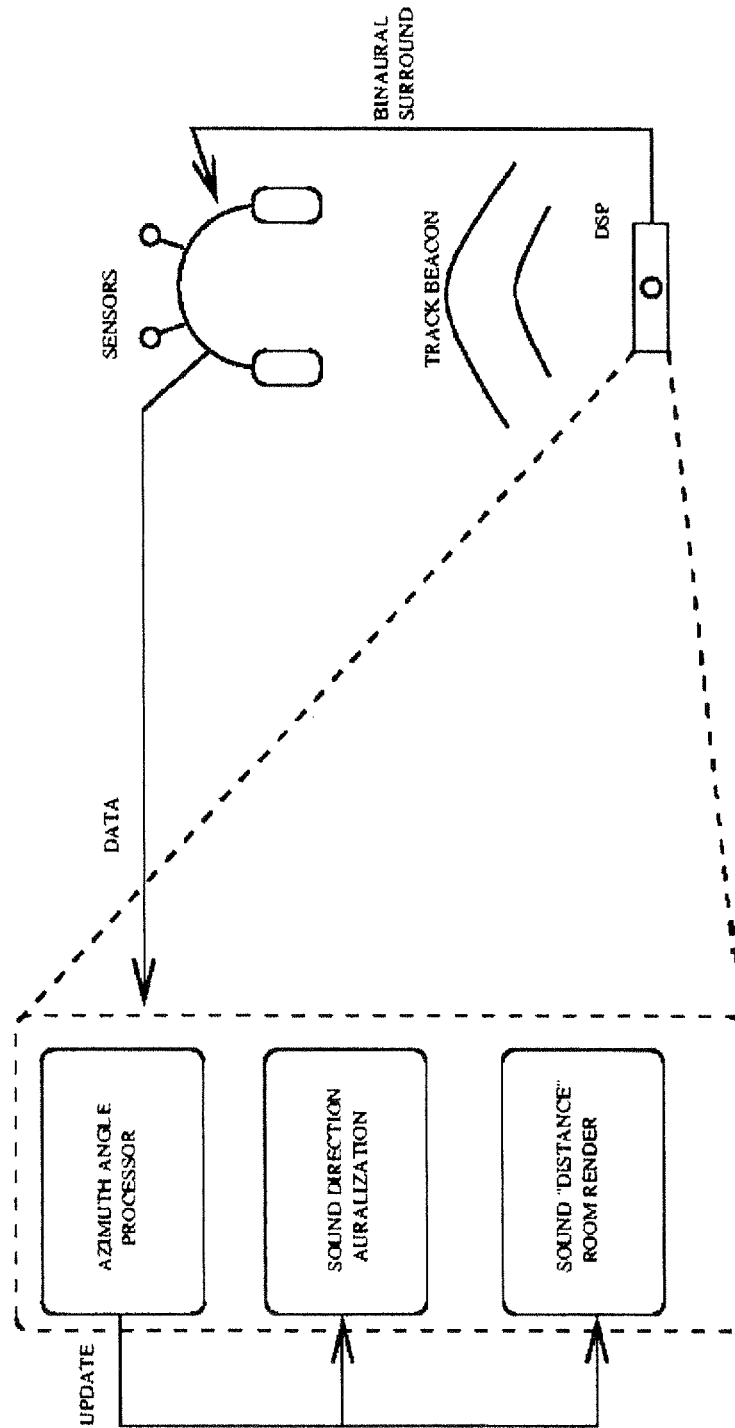
FIG. 6B is a schematic diagram of the hearing aid fitting system illustrated in FIG. 6A.

As further shown in FIG. 6B, the headphones are coupled to a head speaker processor that inputs binaural surround sound to the headphones as well as generates a tracking beacon (e.g., an ultrasonic signal) that is detected by the head-tracker sensors. Data from the sensors is provided to the processor. The processor includes an azimuth angle processor for determining the azimuth angle of the headphones and sound direction auralization. Based on the detected azimuth angle of the headphones by the head-tracker sensors, the sound direction auralization is updated according. As such, a patient wearing the headphones during a fitting session will have the sensation that the source or location of a particular tone is emanating from a direction. As the patient turns to face the source, the sound pressure, phase, delay and/or spectral composition is automatically adjusted in both ears to give the audible sensation that the source is at a fixed direction.

Figure 7:
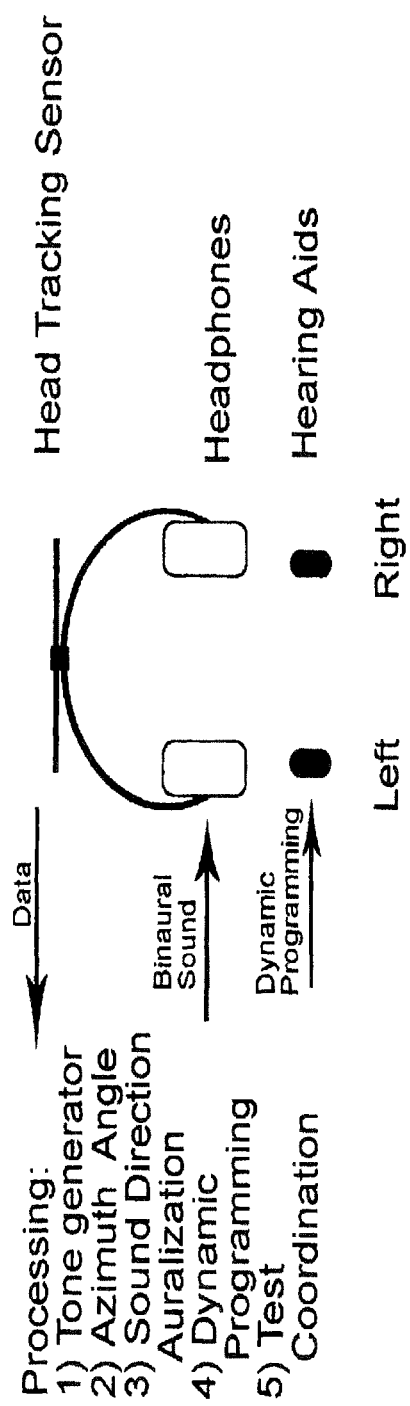
FIG. 7 is a schematic diagram of the steps for performing a method for hearing aid fitting in accordance with the principles of the present invention.

FIG. 7 sets forth the primary process elements of a fitting system in accordance with the present invention. The system includes headphones, a head tracking sensor attached to the headphones, and hearing aid(s) that are dynamically programmable through the headphones (if applicable). Data from the head tracking sensor is sent to the processing unit. The processing unit includes a binaural tone generator, azimuth angle calculator, sound direction auralization, dynamic hearing aid programming capability and test administration and coordination.

A hearing test administered using the foregoing system will reveal the differential sound pressure requirements for the individual for one frequency band-pass at one level of sound input to achieve directional sameness. The data is logged and the appropriate gain compensation curves are modified for each hearing aid for the appropriate frequency band-pass. The appropriate reprogramming is then applied to the hearing aid(s).

This test is successively repeated for applicable softer tone levels. For example, each test may lower the tone input stimulus by 10 dB from the previous measured level. Again, the differential sound pressure requirements are logged and the appropriate gain compensation curves are modified for each hearing aid for the appropriate frequency band-pass. The appropriate reprogramming is then applied to the hearing aid(s). Such small and subtle changes and evaluations are possible because of the speed at which such tests may be made and data evaluated with the protocol of the present invention.

Eventually, the channel volume softness reaches a point where the individual is unable to determine sound direction within a short time, or his/her head searching motions become exaggerated, or he/she states that he/she is no longer able to determine direction, or his/her sensed perception differs significantly from previous measurements, or a combination of the above occurs. This level of softness can also be used to modify the threshold level of hearing for the gain compensation curves, calculations, and hearing aid channel programming. Further changes to the input sound stimulus provided may be made and tests performed to more accurately determine this level. With this protocol, the threshold level of hearing is far more accurately determined and more repeatable than the prior art due to these quantifiable directional measurements.

When measuring hearing thresholds it is easier for the individual to follow a tone that is audible and decreasing in amplitude than to detect a tone that was previously inaudible and detect when the tone becomes audible. This is due to a "top-down" influence, which means that the subject will be expecting to hear the sound and will, therefore, be more motivated with higher levels of concentration.

The test is then successively repeated for louder tone levels (e.g., above the 70 $dB_{SPL}$ initial comfortable level). For example, each test may increase the tone input stimulus by 10 dB from the previous measured level. Again, the differential sound pressure requirements are logged and the appropriate gain compensation curves are modified for each hearing aid for the appropriate frequency band-pass. The appropriate reprogramming is then applied to the hearing aids.

Eventually the channel volume loudness reaches a point where the individual has previously indicated that the sound level is uncomfortably loud, unpleasant or painful. It is not desirable or necessary to continue to increase the sound levels and testing past this point.

The test is then performed again for each of the frequency band-pass channels in order to create coordinated hearing compensation curves for azimuth directional sameness perception for all channels. The test is then randomly re-performed for test verification and authentication. Additional tests and reprogramming are performed as required until repeatability is established. Alternatively, the tests can be performed at fixed stimulus levels for all frequency band-pass channels before changing the stimulus level for a subsequent sets of frequency tests.

Figure 8:
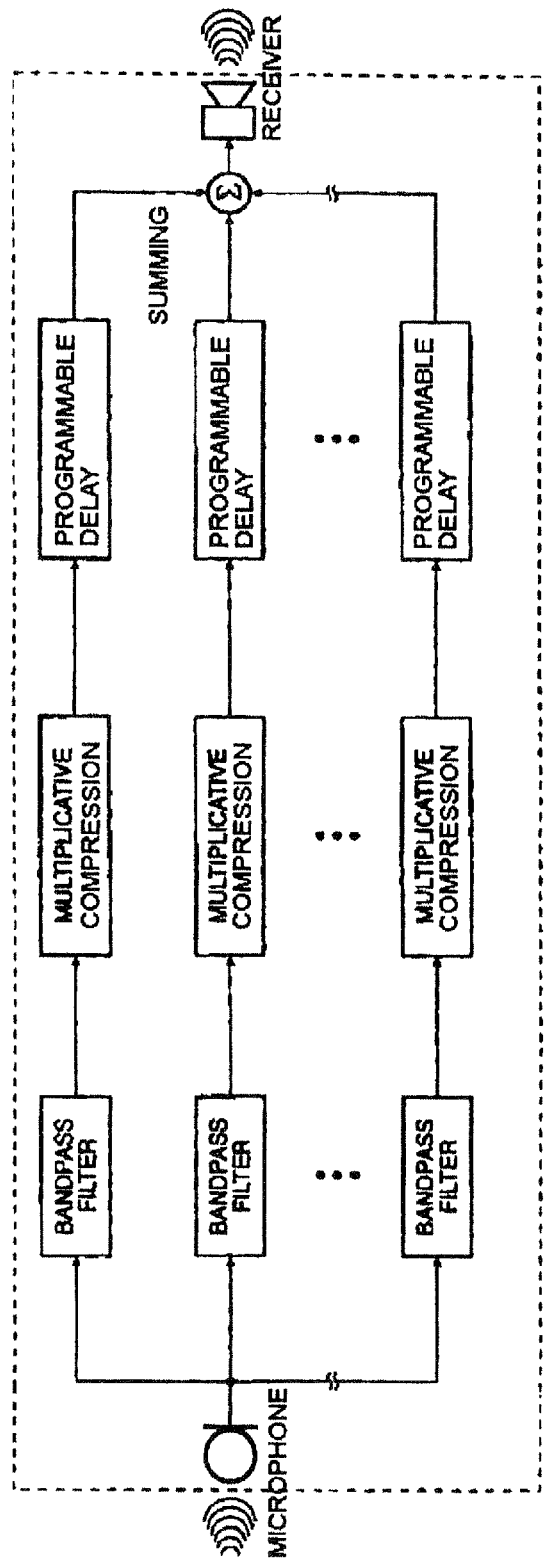
FIG. 8 is a schematic block diagram of the signal processing of a hearing aid to generate programmable delays in accordance with the principles of the present invention.

Multiple channel delay matching for improved speech understanding in noise is then performed. Programmable frequency band delay correction is added to some or all of the frequency band-pass channels in a hearing aid. These delay matching tests require the hearing aids to be worn during testing. The delays are then calibrated and coordinated to yield similar directional response sameness for each frequency band-pass channel as sensed by the hearing aid fitted individual in order to sharpen and align the sensation of delay coordination. The programmable delays are shown in FIG. 8. The programmable delay may be accomplished by means of a programmable length FIFO (First In First Out) digital storage device that is incorporated into the hearing aid.

In a similar manner, pulsed tones or chirps are used to replace the continuous tones used in the preceding tests for delay matching. The pulsed tone tests are given for all band-pass frequency channels. Thus, the pulsed tones are used to coordinate and calibrate each frequency band-pass channel to yield the equivalent azimuth directional delay sameness as the amplitude direction perception and to sharpen and align the directional response sensed by the hearing aid fitted individual. The data is logged and the appropriate programmable delay is programmed as applicable into the hearing aids. It is noted that the gain compensation curves used for amplitude directional fitting may require readjustment based on the results of these tests as the sensation of azimuth source direction may differ for pulsed tones or chirps from that derived for continuous tones.

Current methods of changing amplification by the hearing aid volume controls may unintentionally smear directional perception as the individual changes amplification to suit his/her preferences in a particular ambient sound environment. The hearing aids according to the present invention are provided with tactile detents in the volume controls to allow positioning at discrete rotary positions. Each detent is associated with a specific set of gain compensation curves tailored for the specifically set hearing aid volume. Accordingly, the hearing aids may be switched between families of coordinated gain compensations curves to maintain azimuth directional sameness for multiple volume levels. Other methods of switching between sets of coordinated curves may also be used as are known in the art (e.g. counting the number of button pushes with an audible feedback).

Figure 9:
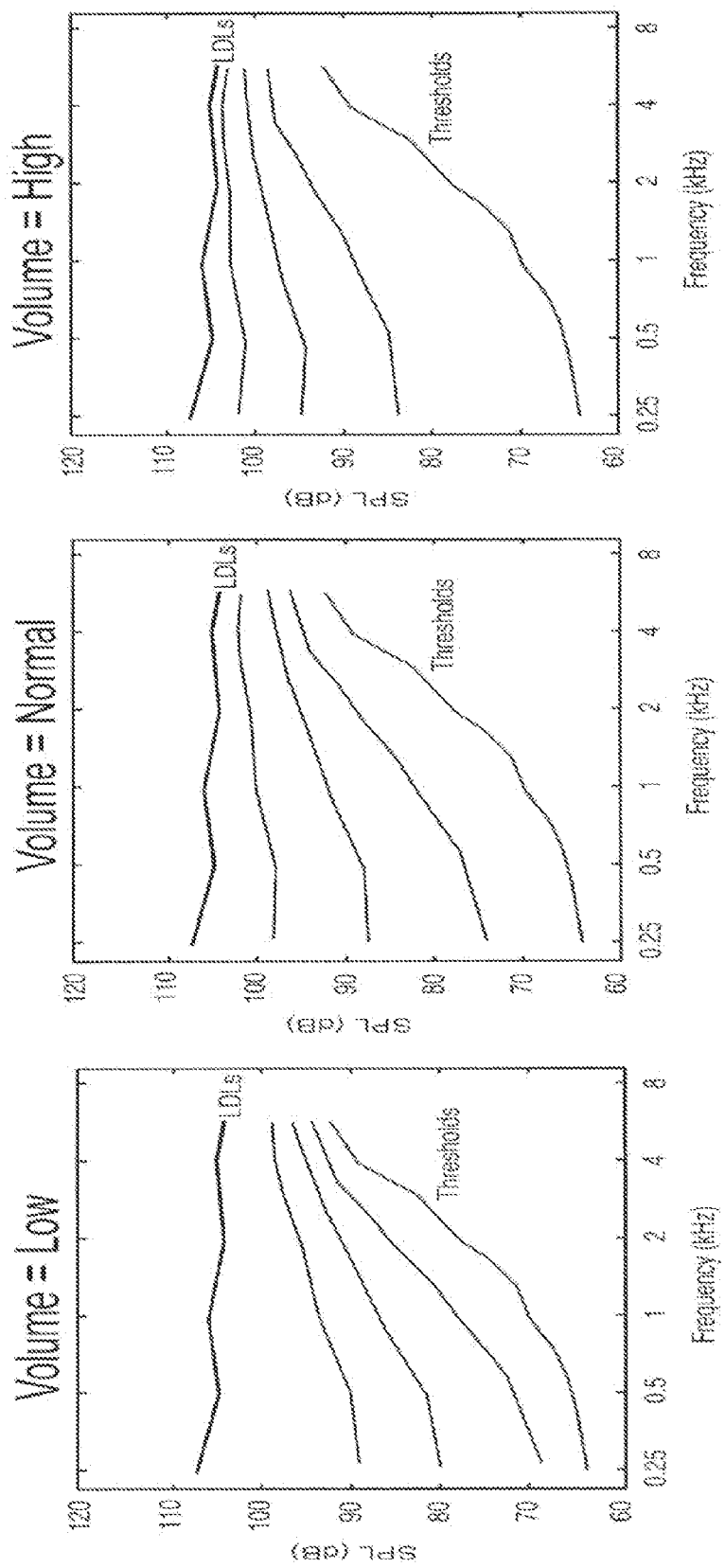
FIG. 9 includes three graphical representations of loudness curves between the thresholds of hearing and the corresponding LDLs.

FIG. 9 illustrates equal loudness levels that might be used to derive the coordinated gain compensations used for a particular hearing aid. Only three equal loudness curves are shown (for simplicity) between the thresholds of hearing and the LDLs. The 3 curves are drawn to demonstrate how the loudness population densities might be altered for the 3 loudness levels selected by the individual. The minimal time required to performing the above tests at 5 or 10 dB increments would be a distinct advantage over the prior art to enable the creation of such a detailed and calibrated fitting and curve families. The appropriate switchable families of compensation curves are then programmed as applicable into the hearing aids. Many more levels of amplification are anticipated under the scope of the present invention. Other methods of switching between coordinated families of gain compensation are also envisioned.

The primary advantage represented by the "Volume=Normal" graph of FIG. 9 is the maximization of meaningful information content within the individual's available dynamic hearing range. The maximization is then used to create the family of hearing compensation curves which are then used to program gain in each of the individual band-pass frequency channels.

The primary advantage shown in the "Volume=Low" graph of FIG. 9 is to reduce the overall SPL when the individual is in a quiet sound environment and S/N is adequate for speech understanding at these overall reduced SPL levels. The purpose here is to provide an overall volume level which is more comfortable for the individual in the low noise environment.

The primary advantage shown in the "Volume=High" graph of FIG. 9 is to increase the overall SPL when the individual is in a very noisy sound environment and bone transfer is interfering and competing for adequate speech understanding.

Figure 10:
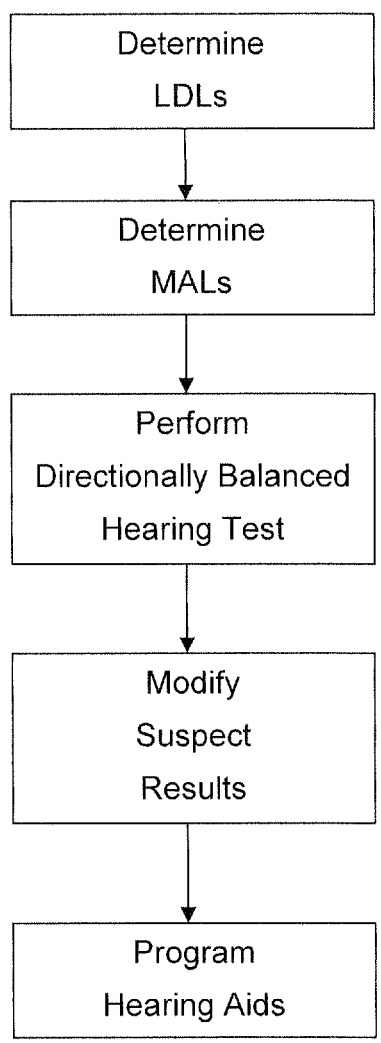
FIG. 10 is a schematic block diagram of an alternative embodiment of a method of performing a hearing aid fitting in accordance with the principles of the present invention.

In another embodiment, as illustrated in FIG. 10, as part of the directional fitting protocols, the present invention also provides a method of testing patients that suffer from loudness recruitment and adjusting the hearing aid gain curves according to the test results. In order to do so, the Loudness Discomfort Levels (LDLs) of the patient are determined by sending a plurality of tones to the patent at various frequencies. The dB level of each tone is increased until the LDL is reached, at which point the patient will signal to the person administering the test that the LDL has been reached or be able to provide a computer input, such as a mouse click or a key press that the LDL has been reached. Likewise, the patient's threshold of hearing is determined by testing for the Minimum Audible Levels (MALs) at each tested frequency. The patient will signal when the tone becomes too soft or when the tone is no longer audible, as the case may be. Finally, the patient is provided a plurality of binaural tones at specific frequencies (e.g., 125 Hz, 250 Hz, 500 Hz, 750 Hz, 1000 Hz, 1500 Hz, 2000 Hz, 3000 Hz, 4000 Hz, 6000 Hz, 8000 Hz, etc.). Ideally, the specific frequencies would match the programmable frequency band-passes of the particular hearing aid to be programmed. Each frequency is provided through the headphones to the patient at various sound pressure levels. The patient then turns in order to face a location where the perceived sound levels in each ear are the same. The gain in each ear is then recorded. Any suspect results can be modified or retested to ensure accuracy of the testing procedure. In order to remove ambiguity of test results when compared to other reporting schemes, attenuation of a fixed sound level stimulus is used (e.g., 110 $dB_{SPL}$). The sound level is then attenuated in precise dB increments between the patient's LDL and MAL (e.g., 10 dB, 20 dB, 30 dB, 40 dB, 50 dB, 60 dB, 70 dB, etc.). For frequencies between the tested frequencies and for sound levels between the attenuated sound levels of the test, the recorded data can be interpolated. While linear interpolation may be sufficiently adequate, other more complex forms of interpolation may also be employed in order to provide more accurate interpolation between data points. Obviously, the greater the number of tested frequencies and sound levels, the more accurate any interpolation of the resulting data will be. Such a number will be limited to a large extent by the time it takes to test a patient using the testing method of the present invention. The processes for directional fitting and recruitment compensation can therefore be identical and both issues can be addressed with the single protocol of the present invention.

Table 1 sets forth data obtained using a directional fitting method according to the present invention on an actual patient. The first recorded number in each column represents data for the left ear and the second recorded number represents the right ear.

measured and recorded. The patient is then subjected to a plurality of tones at specific frequencies at various attenuated sound levels. As the patient rotates their head in order to achieve perceived directional sameness between the left and right ears for each tone, the difference in actual sound pressure levels are recorded and the difference calculated. In order to help eliminate data errors that could occur due to repetitive behavior, the system is configured to change the azimuth location of actual equalized sound so that the patient does not return to the exact same location for each tone in order to achieve perceived sound equalization between the left and right ears. It is interesting to note that the entire test to obtain all of the data set forth in Table 1 took less than fifteen minutes. The LDL and MAL results each took approximately three minutes and the directionally balanced hearing test took approximately nine minutes, with each set of tones for a given $dB_{SPL}$ level taking on average approximately one and a half to two minutes depending on the number of individual tests. As such, the method of directional fitting and recruitment compensation according to the present invention can be performed more quickly than current testing methods that often take several hours and with better results that ultimately increase the perceived S/N for the patient and patient satisfaction.

As shown in Table 1, the patient was able to detect a tone at 500 Hz with 70 dB of attenuation of a 110 $dB_{SPL}$ sound source. Sounds at other frequencies at this level of attenuation were not detectable. As the attenuation decreased, the patient was able to hear the lower frequency tones, but the higher frequency tones were only audible at significantly higher $dB_{SPL}$ levels. Because of the patients preset LDLs, sounds with only 10 dB of attenuation were not presented to the patient. The overall number of tests required was thusly reduced. As the patient was subjected to the various tones, the sound pressure levels for balanced perception for the

TABLE 1

| STIMULUS 110 dB SPL | 10 dB | | | 20 dB | | | 30 dB | | | 40 dB | | | 50 dB | | |
|---|---|---|---|---|---|---|---|---|---|---|---|---|---|---|---|
| 125 Hz | — | — | — | 19.1 | 20.9 | 1.7 | 27.4 | 32.6 | 5.2 | 34.6 | 45.4 | 10.9 | 43.8 | 56.2 | 12.5 |
| 250 Hz | — | — | — | 21.5 | 18.5 | 3.0 | 29.0 | 31.0 | 1.9 | 40.0 | 40.0 | 0.1 | 39.5 | 60.5 | 21.0 |
| 500 Hz | — | — | — | — | — | — | 27.3 | 32.7 | 5.4 | 36.9 | 43.1 | 6.2 | 46.6 | 53.4 | 6.8 |
| 750 Hz | — | — | — | — | — | — | 26.4 | 33.6 | 7.2 | 36.5 | 43.5 | 7.1 | 47.2 | 52.8 | 5.7 |
| 1000 Hz | — | — | — | — | — | — | 25.8 | 34.2 | 8.4 | 35.1 | 44.9 | 9.9 | 46.8 | 53.2 | 6.5 |
| 1500 Hz | — | — | — | 19.9 | 20.1 | 0.1 | 28.9 | 31.1 | 2.2 | 38.6 | 41.4 | 2.8 | 45.7 | 54.3 | 8.7 |
| 2000 Hz | — | — | — | 17.9 | 22.1 | 4.2 | 29.9 | 30.1 | 0.3 | 38.6 | 41.4 | 2.8 | 47.7 | 52.3 | 4.6 |
| 3000 Hz | — | — | — | 18.0 | 22.0 | 4.0 | 29.2 | 30.8 | 1.5 | 38.8 | 41.2 | 2.3 | 45.4 | 54.6 | 9.3 |
| 4000 Hz | — | — | — | 15.9 | 24.1 | 8.2 | 27.5 | 32.5 | 5.0 | 36.4 | 43.6 | 7.1 | 50.0 | 50.0 | 0.0 |
| 6000 Hz | — | — | — | 18.2 | 21.8 | 3.5 | 29.4 | 30.6 | 1.3 | 39.2 | 40.8 | 1.6 | — | — | — |
| 8000 Hz | — | — | — | 22.4 | 17.6 | 4.8 | 33.6 | 26.4 | 7.2 | 44.6 | 35.4 | 9.3 | — | — | — |

| STIMULUS 110 dB SPL | 60 dB | | | 70 dB | | | Loudness Discomfort Levels | | Threshold of Hearing | |
|---|---|---|---|---|---|---|---|---|---|---|
| 125 Hz | 59.6 | 60.4 | 0.7 | — | — | — | 13.7 | 18.3 | 61.3 | 61.4 |
| 250 Hz | 57.5 | 62.5 | 4.9 | — | — | — | 11.3 | 18.9 | 44.1 | 63.7 |
| 500 Hz | 57.9 | 62.1 | 4.3 | 68.4 | 71.6 | 3.3 | 22.3 | 26.4 | 64.0 | 70.4 |
| 750 Hz | 57.5 | 62.5 | 5.1 | — | — | — | 23.7 | 29.4 | 65.6 | 65.1 |
| 1000 Hz | 58.5 | 61.5 | 2.9 | — | — | — | 20.3 | 28.0 | 57.4 | 66.3 |
| 1500 Hz | 56.7 | 63.3 | 6.7 | — | — | — | 19.9 | 28.9 | 59.4 | 64.2 |
| 2000 Hz | 57.6 | 62.4 | 4.9 | — | — | — | 19.2 | 24.4 | 62.3 | 63.5 |
| 3000 Hz | — | — | — | — | — | — | 13.7 | 20.4 | 51.7 | 54.8 |
| 4000 Hz | — | — | — | — | — | — | 16.1 | 27.7 | 52.7 | 52.7 |
| 6000 Hz | — | — | — | — | — | — | 14.0 | 13.9 | 39.6 | 40.7 |
| 8000 Hz | — | — | — | — | — | — | 23.0 | 16.2 | 48.1 | 40.7 |

In a first step, the Loudness Discomfort Levels of the patient are recorded individually for both the left and right ears. Next, the Thresholds of Hearing or MAL levels are right and left ears were recorded. The difference between the left and right ears is then used to program the gain curves of the hearing aids. In some cases, the difference was more than 10 dB$_{SPL}$. Such a significant difference, if not accounted for (as is the case in current methods of hearing aid fitting), will result in the patient's inability or at least diminished ability to filter out sounds that are not emanating from a desired sound source, such as the speech of a person with whom the patient is conversing. By achieving directional sameness across a broad range of frequencies and sound levels within the dynamic range of the patient, the patient will then be able to focus on, for example a conversation, that is directly ahead and mentally dismiss sounds that are emanating from the sides or from behind the patient. By using such directional sameness techniques of the present invention with hearing aids that employ directional microphones, the patient may even achieve "super hearing" that has not been possible heretofore.

In addition, because the test is structured to accommodate the patient's LDLs, the hearing aids can be programmed to limit sounds that exceed the LDLs across all frequencies. This is particularly important for patients suffering from loudness recruitment conditions. Accordingly, the patient's exposure to perceived over-amplification is significantly reduced if not completely eliminated resulting in a more pleasant experience, especially when using the hearing aids in noisy environments.

It is interesting to note in the patient's data of Table 1 that at certain frequencies, e.g., 8000 Hz, the gain requirements to equalize the sound between the left and right ears reversed. That is, the patient required an increase in gain in the right ear at 8000 Hz while requiring the additional gain to be present in the left ear at almost all other frequencies for a given dB level. Knowing this, allows the hearing aids to be programmed to take this into account so that when exposed to frequencies at or near 8000 Hz, the hearing aid will adjust the gain accordingly.

As the various tones are presented to the patient, the patient is asked to rotate his or her head by either turning the head from side-to-side or rotating in a chair until the right and left ear tones are perceived to be at equal volume by the patient. As the patient rotates their head, the sound level presented to each ear is correspondingly adjusted. For example, if the sound in the left ear is perceived as being a lower volume than the sound coming to the right ear, the person would instinctively turn their head to the right unit the sound in both ears is equalized. At this point, the patient would signal to the test administrator (which could be a person or could be computer software) that perceived equalization of sound has been achieved. The test administrator may also determine independently that equalization has been achieved by watching for the minimization of the patients source seeking head/chair motions. The system will then record the sound levels being presented to the left and right ears and calculate the difference. The process is repeated for each frequency and for each level of attenuation in the test. The differences are then used to generate gain curves for programming the patient's hearing aids, which now accommodate for the patient's specific loudness recruitment condition.

Knowing the LDL of the patient at each of the tested frequencies has the added benefit of allowing the system to program the hearing aids to accommodate the patient's specific LDL at each frequency. Accordingly, for sounds that exceed the LDL, the hearing aids can be used to attenuate the sounds. Such amplification and compression techniques thus allow the hearing aid to amplify sounds that are below the LDL of the patient and attenuate sounds that exceed the LDL while providing smooth transitions between stimulus levels and also maintaining directional perception. The resulting gain curves are configured to compensate for the specific MAL and LDL levels of the patient. Accordingly, the directional fitting techniques of the present invention are employed to provide amplification and compression of sound by the hearing aids that are within the dynamic range of the patient and thus tailored to account for the patient's specific loudness recruitment condition. It is readily apparent that the approach of the present invention can be used to maximize information content of the audio signal to match the patient's remaining reduced dynamic hearing range.

Another method of obtaining directional sameness according to the directional fitting techniques of the present invention is to place the patient in a darkened room and to simulate directional perception by altering the gain levels between ears and/or phase delays in sounds presented to the patient. With the patient's eyes closed, a series of tones are presented to the patient. If the tones are perceived as being louder in one ear, the patient is provided with a user controllable interface, such as a joystick, wheel, or slide pot that allows the user to adjust the gain levels in order to reach a point where the perceived loudness levels in each ear are equal. When perceived equalization has been achieved, the patient can then press a button to cause the system to move to the next tone in the test or the system can determine adjustments are no longer being made and assume balance has been achieved and move to the next test automatically. The difference in sound pressure levels for the tested tone is then recorded by the system and the difference used to program the hearing aid as previously described herein.

Likewise, in another testing phase, the patient could be presented with a series of sound clicks. The clicks presented to the patient are slightly out of phase so that the patient will hear the click in one ear before the other. As the clicks are repeated, the user is provided with a user interface that allows the user to control the timing of the clicks in an attempt to bring the clicks into synchronization. This data is then used to program phase delays into the hearing aids as may be needed in order to correct deficiencies in sound localization of the patient.

Thus, rather than requiring the patient to physically move their head and to adjust the gain or phase delay in each ear based upon detecting the head movement of the patient, the system could be configured to allow the user to directly interface with the system through a user input to alter the test parameters (e.g., sound pressure, phase delay, etc.) during the test in order to achieve the same results. Thus, while the present invention has been described with reference to directional fitting of hearing aids, the invention is not intended to be limited to systems that require the patient being tested to reorient their head or body to face a perceived sound source. Once the hearing aid fitting is complete, the testing may be repeated to ensure the accuracy of the fitting. Any adjustments to the gain curves can then be made to fine tune the hearing aids in order to obtain directional sameness for all frequencies within the dynamic range of the patient.

One significant improvement in the art of hearing aids is a direct result of the testing method of the present invention. Once the patient's hearing aids are programmed based on the data obtained using the directional fitting technique of the present invention, the patient wearing the hearing aids can more easily locate the source of a particular sound and the S/N is improved by at least 3 dB or more. It has been noted in the art that hearing aid companies may spend $100,000 or more in research and development to increase the S/N of a hearing aid by 0.1 dB. The directional fitting techniques of the present invention present a major step in improving the perceived S/N of hearing aids without requiring additional investment in the technology of the hearing aid itself. That is, the directional fitting techniques of the present invention are compatible with existing hearing aid technologies and can be adapted to program any brand of digital hearing aid that employs the use of programmable gain curves to adjust amplification at various frequencies.

Variations and combinations of the above techniques are also possible. Other compression techniques taught in the current art may also be used.

It is important to realize that the protocol creates left and right data pairs for coordinated directional perception. A frequency/amplitude data point for the left side is consequently tied to a corresponding data point for the right side (and vice versa). Therefore, the hearing compensation curves can be created for either the left or right side independently and the opposite side becomes a dependant creation.

The tester or test administrator as defined in the above protocol need not be an audiologist or even a person, but could be a software program running the protocol. Thus, the protocol is also suitable for autonomous interaction with the individual using the internet, a personal computer or additional computation and interface capabilities built into the fitting system such as controls to establish the initial comfortable hearing level, a control to indicate the user has reached the loudness discomfort level, a control to indicate the level is below the threshold of hearing or other controls as may appear obvious to one skilled in the art. Such controls may include a computer mouse and computer generated user interface by which the user can click on a specific button to indicate a particular condition during the testing procedure (e.g., click a button when a loudness discomfort level is reached).

It is also contemplated that the low noise environment (<30 $dB_{SPL}$) may be created artificially with noise cancellation headphones or other masking techniques. The hearing aids can be reprogrammed through electrical wires attached to the hearing aids using existing technologies such as a HiPRO programming device. The hearing aids may also be reprogrammed using audio reprogramming according to the present invention.

Time Domain Audio Frequency Shift Keying (FSK), Audio Pulse Position Modulation (PPM), Audio Pulse Code Modulation (PCM) or Audio Pulse Width Modulation (PWM) or other similar information encoding technology within the audio channel may be used for programming the hearing aids by designing such features into the hearing aids and incorporating decoding into one or more of the audio channels. Programming then occurs through the headphones or even potentially through a telephone receiver. The hearing aid may be preprogrammed as a left or right hearing aid and may also have a serial number or other keying system or other encryption technology so that programming is individualized for a particular hearing aid and cannot be performed by systems and/or individuals not authorized by the manufacturer. Such a system of programming is preferred for an autonomous protocol. Such a system is preferred in the first 30 days of fitting as the user adapts to the new hearing aids and reprogramming is warranted. Such a system is preferred when re-fitting is performed periodically or as required when the user feels the fitting is now suboptimal. It is also contemplated that a wired or wireless communication with the hearing aids may be employed, such as through a USB cable or Blue Tooth communication.

A fiber optic waveguide may also be added to the hearing aid. During the actual hearing aid fitting, the fiber optic waveguide is used in conjunction with an external laser, detector, optics and processor to measure the receiver diaphragm velocity using interference techniques as is know in the art to determine the spectral profile response in the specific acoustical environment such as when the hearing aid is inserted into the ear canal or when using the specific unique sound chamber moldings required. The necessary pre-distortion is then included with the required band specific amplification for hearing aid programming and stored in the hearing aid processor. The fiber optic waveguide is then removed or broken off for normal use by the wearer.

The present invention provides dynamic programming of the hearing aid during the audiometrical protocol described herein. Programming of the hearing aid only at the conclusion of the protocol is also anticipated. Programming of the hearing aid at intervals during the protocol is also anticipated.

The present invention also provides programming of the hearing aid through signals supplied in the audio channel. Such programming is superior to the art which uses a physical electronic interface. Audio channel programming also removes the requirement of making such electrical connections by the individual in the autonomous fittings situation.

Although the binaural fitting of a pair of hearing aids are described herein, it is anticipated that the individual may only require a single hearing aid for one ear. The methods of fitting hearing aids utilizing head azimuth measurement and directional fitting provided herein are still applicable. For such cases, it is still important to realize that the protocol creates left and right data pairs for coordinated directional perception and that a frequency/amplitude data points for the left side are still tied to corresponding data points for the right side. For the individual requiring only a single hearing aid, the hearing compensation curves for the single hearing aid will be dependant on independent data points for the ear that does not require a hearing aid.

It would be apparent to those skilled in the art that some other method of determining head azimuth, or other modifications could be employed in a similar manner for directional testing without departing from the inventive concepts herein. Thus, while there have been described various embodiments of the present invention, those skilled in the art will recognize that other and further changes and modifications may be made thereto without department from the spirit of the invention, and it is intended to claim all such changes and modifications that fall within the true scope of the invention. It is also understood that, as used herein and in the appended claims, the singular forms "a," "an," and "the" include plural reference, unless the context clearly dictates otherwise.

Unless defined otherwise, all technical and scientific terms used herein have the same meanings as commonly understood by one of ordinary skill in the art to which this invention belongs. While various methods and structures of the present invention are described herein, any methods or structures similar or equivalent to those described herein may be used in the practice or testing of the present invention. All references cited herein are incorporated by reference in their entirety and for all purposes. In addition, while the foregoing advantages of the present invention are manifested in the illustrated embodiments of the invention, a variety of changes can be made to the configuration, design and construction of the invention to achieve those advantages including combinations of components of the various embodiments. Hence, reference herein to specific details of the structure and function of the present invention is by way of example only and not by way of limitation.

What is claimed is:

1. A system for programming at least one hearing device, comprising:
   stereo headphones having a first speaker configured for positioning relative to a first ear of a user and a second speaker configured for positioning relative to a second ear of a user;
   a processing device electronically coupled to the stereo headphones, wherein the processing device is configured to simultaneously provide a first audible tone through the first speaker of the stereo headphones and a second audible tone through the second speaker of the stereo headphones, wherein the first audible tone has a first sound pressure level and wherein the second audible tone has a second sound pressure level;
   a user controllable interface electronically coupled to the processing device, the user controllable interface configured to allow a user to adjust the first sound pressure level of the first audible tone to a first adjusted sound pressure level so that the user perceives the first adjusted sound pressure level of the first audible tone to be substantially balanced with the second sound pressure level of the second audible tone, the processing device further configured to record at least one first datum representing a difference between the first adjusted sound pressure level and the second sound pressure level; and
   a programming interface configured to receive the at least one first datum and for programming at least one hearing device based on the at least one first datum according to the difference between the first adjusted sound pressure level and the second sound pressure level.

2. The system of claim 1, wherein the processing device comprises a computer system.

3. The system of claim 1, wherein the user controllable interface comprises one or more buttons.

4. The system of claim 1, wherein the at least one hearing device comprises at least one hearing aid.

5. The system of claim 1, wherein the programming interface is further configured to program the at least one hearing device based on a first set of data representing a set of differential sound pressure levels derived from the user's perception of substantial balance between the first adjusted sound pressure level of the first audible tone and the second sound pressure level of the second audible tone at each of a plurality of frequencies.

6. The system of claim 5, wherein the programming interface is further configured to program the at least one hearing device based on a second set of data representing a set of loudness discomfort levels of the user at each of a plurality of frequencies.

7. The system of claim 6, wherein the programming interface is further configured to program the at least one hearing device based on a third set of data representing a set of minimum audible levels of the user at each of a plurality of frequencies.

8. The system of claim 1, wherein the programming interface is configured to program the at least one hearing device by adjusting at least one amplification setting of the at least one hearing device.

9. The system of claim 1, wherein the programming interface is configured to program the at least one hearing device by programming at least one hearing compensation curve for the at least one hearing device.

10. A system for programming at least one hearing device, comprising:
    stereo headphones having a first speaker configured for positioning relative to a first ear of a user and a second speaker configured for positioning relative to a second ear of a user;
    a processing device electronically coupled to the stereo headphones, the processing device configured to simultaneously provide a first audible tone through the first speaker of the stereo headphones and a second audible tone through the second speaker of the stereo headphones, the first audible tone having a first sound pressure level and the second audible tone having a second sound pressure level;
    a user controllable interface electronically coupled to the processing device, the user controllable interface configured to allow a user to adjust the first sound pressure level of the first audible tone to a first adjusted sound pressure level and to adjust the second sound pressure level of the second audible tone to a second adjusted sound pressure so that the user perceives the first adjusted sound pressure level of the first audible tone to be substantially balanced with the second adjusted sound pressure level of the second audible tone, the processing device further configured to record at least one first datum representing a difference between the first adjusted sound pressure level and the second adjusted sound pressure level; and
    a programming interface configured to receive the at least one first datum and for programming at least one hearing device based on the at least one first datum representing the difference in sound pressure level between the first adjusted sound pressure level and the second adjusted sound pressure level.

11. The system of claim 10, wherein the processing device comprises a computer system.

12. The system of claim 10, wherein the user controllable interface comprises one or more buttons.

13. The system of claim 10, wherein the at least one hearing device comprises at least one hearing aid.

14. The system of claim 10, wherein the programming interface is further configured to program the at least one hearing device based on a first set of data representing a set of differential sound pressure levels derived from the user's perception of substantial balance between the first adjusted sound pressure level of the first audible tone and the second adjusted sound pressure level of the second audible tone at each of a plurality of frequencies.

15. The system of claim 14, wherein the programming interface is further configured to program the at least one hearing device based on a second data set representing a set of loudness discomfort levels of the user at each of a plurality of frequencies.

16. The system of claim 15, wherein the programming interface is further configured to program the at least one hearing device based on a third data set representing a set of minimum audible levels of the user at each of a plurality of frequencies.

17. The system of claim 10, wherein the programming interface is configured to program the at least one hearing device by adjusting at least one amplification setting of the at least one hearing device.

18. The system of claim 10, wherein the programming interface is configured to program the at least one hearing device by programming at least one hearing compensation curve into the at least one hearing device.

19. A system for acoustically fitting a hearing aid, comprising:

stereo headphones electronically coupled to a processing device, the processing device configured to simultaneously provide through the stereo headphones a first tone through a first channel of the stereo headphones and a second tone through a second channel of the stereo headphones, the first tone having a first frequency and a first sound pressure level and the second tone having a second frequency and a second sound pressure level;

a controllable interface electronically coupled to the processing device, the controllable interface configured to allow a test administrator to vary the first sound pressure level of the first tone to a first adjusted sound pressure level of the first tone, the first adjusted sound pressure level of the first tone corresponding to a sound pressure level where a patient signals to the test administrator that the patient perceives through the stereo headphones that the first adjusted sound pressure level of the first tone is substantially audibly balanced with the second sound pressure level of the second tone;

a recording device for recording at least one differential sound pressure based on at least the first adjusted sound pressure level; and a hearing aid programming interface wherein the hearing aid programming interface is configured to program at least one gain compensation curve into at least one hearing aid, the gain compensation curves being a function of the recorded at least one differential sound pressure.

20. The system of claim 19, wherein the at least one gain compensation curve is based on a first recorded data set comprising a set of loudness discomfort levels of the patient at each of a first plurality of frequencies of at least one of the first and second tones and is further based on a second recorded data set comprising a set of minimum audible levels of the patient at each of a second plurality frequencies of at least one of the first and second tones.

21. The system of claim 1, wherein the user controllable interface comprises a dial.

22. The system of claim 10, wherein the user controllable interface comprises a dial.

* * * * *